US008628569B2

(12) United States Patent
Benichou et al.

(10) Patent No.: US 8,628,569 B2
(45) Date of Patent: Jan. 14, 2014

(54) IMPLANTABLE PROSTHETIC VALVE ASSEMBLY AND METHOD FOR MAKING THE SAME

(75) Inventors: Netanel Benichou, D.N. Hof HaCarmel (IL); Benjamin Spenser, D.N. Hof HaCarmel (IL); Assaf Bash, Benyamina-Givat Ada (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/569,028

(22) Filed: Aug. 7, 2012

(65) Prior Publication Data

US 2012/0303113 A1 Nov. 29, 2012

Related U.S. Application Data

(63) Continuation of application No. 11/644,517, filed on Dec. 22, 2006, now Pat. No. 8,236,045.

(51) Int. Cl.
*A61F 2/24* (2006.01)
(52) U.S. Cl.
USPC .......... 623/2.1; 623/1.26; 623/2.18; 623/2.17

(58) Field of Classification Search
CPC ..................................... A61F 2/2412
USPC ................................. 623/2.1–2.19
See application file for complete search history.

(56) References Cited

U.S. PATENT DOCUMENTS

2003/0114913 A1* 6/2003 Spenser et al. ............... 623/1.11
2005/0137690 A1* 6/2005 Salahieh et al. .............. 623/2.11

* cited by examiner

*Primary Examiner* — Jason-Dennis Stewart
(74) *Attorney, Agent, or Firm* — Pui Tong Ho; David L. Hauser

(57) ABSTRACT

An implantable prosthetic valve assembly having a support stent, or frame, having circumferential struts with multiple bends forming obtuse angles when the valve assembly is expanded to its functional size. The frame can be manufactured with one or more of the circumferential struts in a partially collapsed state and a flexible valve member can be mounted to the partially collapsed frame. The partially collapsed struts can be formed with multiple bends having angles selected to facilitate crimping of the frame to a profile suitable for percutaneous delivery. When the frame is expanded, the bends can expand to form obtuse angles, thereby enhancing the rigidity of the frame to better resist closing forces exerted on the valve assembly.

26 Claims, 10 Drawing Sheets

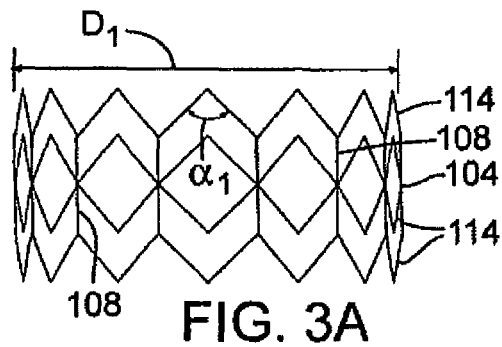
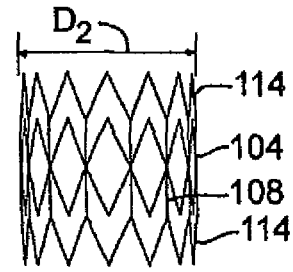
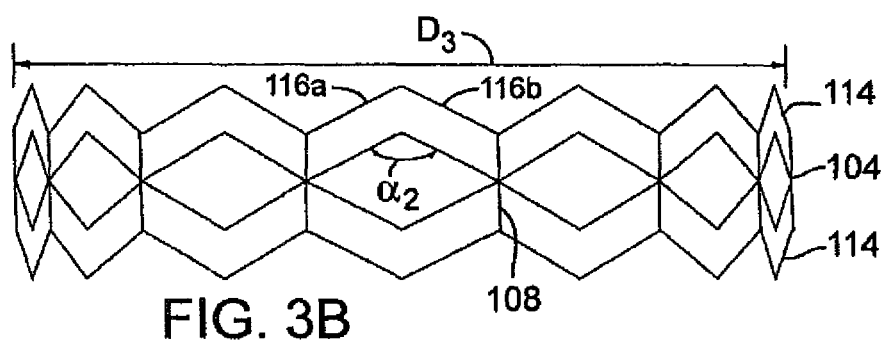
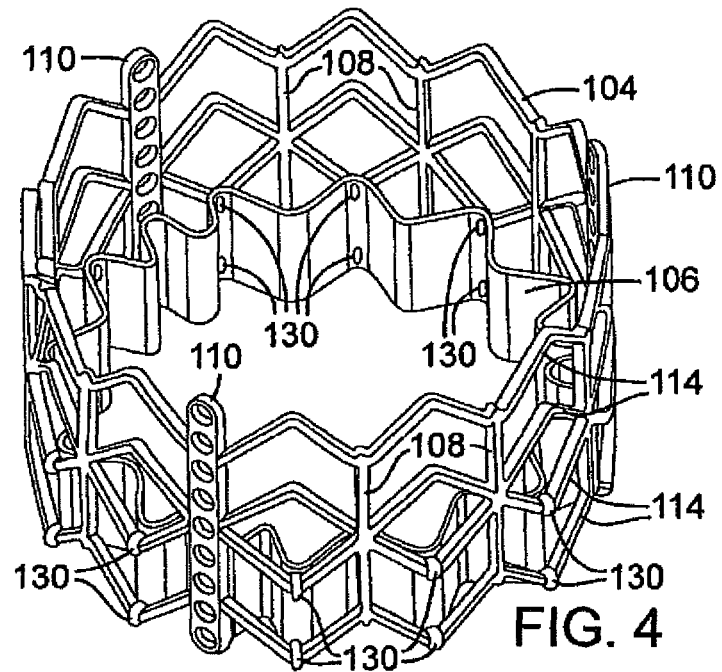

IMPLANTABLE PROSTHETIC VALVE ASSEMBLY AND METHOD FOR MAKING THE SAME

RELATED APPLICATIONS

The present application is a continuation of U.S. application Ser. No. 11/644,517, filed Dec. 22, 2006, now U.S. Pat. No. 8,236,045.

FIELD

The present disclosure concerns embodiments of an implantable prosthetic valve and method for making the same.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise and even death. For many years, the definitive treatment for such disorders was the surgical repair or replacement of the valve during open heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic heart valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

FIG. 1 shows a known percutaneous heart valve 10 in its deployed or expanded state. The valve 10 comprises a flexible prosthetic valve member 12 attached to an expandable frame, or support stent, 14 with sutures 16. The frame 14 includes angularly-spaced, axial struts 18 and circumferentially extending, zig-zag struts 20 secured to the axial struts 18. Between each pair of axial struts 18, each strut 20 comprises two linear strut members 22a, 22b forming a bend in the strut to facilitate crimping of the valve 10 to a smaller diameter for percutaneous delivery of the valve. As can be appreciated, the easiest and most straightforward way of attaching the valve member 12 to the frame 14 is when both the frame 14 and the valve member 12 are in the expanded state shown in FIG. 1. The assembled valve 10 typically is stored in the expanded state or a partially crimped state and then fully crimped to a much smaller profile in the operating room just prior to implantation.

An important characteristic of a percutaneous prosthetic heart valve is its ability to be crimped to as small diameter as possible to permit the crimped valve to be advanced through the blood vessels to an implantation site. Another important characteristic of a percutaneous heart valve is its ability to retain an expanded shape once implanted. To maximize circumferential and radial rigidity of the valve frame, and therefore enhance the ability of the frame to retain an expanded shape once implanted, it is desirable to maximize the angle θ between strut members 22a, 22b. Ideally, the struts 20 should be nearly circular (i.e., the angles θ are slightly less than 180 degrees) to provide maximum rigidity. Moreover, by increasing the rigidity of the struts, less metal can be used for forming the frame, which allows the valve to be crimped to a smaller profile.

Unfortunately, forming the struts 20 with angles θ that are greater than 90 degrees can lead to uneven and unpredictable crimping. Thus, if the valve assembly is assembled in its expanded, functional shape, then in order to permit even and predictable crimping of the frame to a predetermined profile suitable for percutaneous delivery, rigid struts with obtuse angles θ cannot be utilized.

SUMMARY

In one aspect, the present disclosure concerns an implantable prosthetic valve assembly having a support stent, or frame, having circumferential struts with multiple bends forming obtuse angles when the valve assembly is expanded to its functional size. The frame can be manufactured with one or more of the circumferential struts in a partially collapsed state and a flexible valve member can be mounted to the partially collapsed frame. The partially collapsed struts can be formed with multiple bends having angles selected to facilitate crimping of the frame to a profile suitable for percutaneous delivery. When the frame is expanded, the bends can expand to form obtuse angles, thereby enhancing the rigidity of the frame to better resist closing forces exerted on the valve assembly (for example, the recoil force exerted on the frame by the distorted stenosed native valve orifice). In particular embodiments, the bends of at least some of the struts when expanded form obtuse angles that are at least about 120 degrees or greater.

In an exemplary embodiment, the frame is manufactured in a partially collapsed state having a generally tubular shape, and a valve member, such as a tricuspid valve member, is attached to the partially collapsed frame. The partially collapsed frame has plural, axial spaced circumferential struts formed with multiple bends that have angles selected to facilitate crimping of the valve assembly to a smaller diameter and that expand to obtuse angles when the valve member is expanded to its functional size. In certain embodiments, for example, the partially collapsed frame is formed with bends having acute angles and expanding the frame forms bends that are at least about 120 degrees. The frame desirably can be crimped to a diameter of about 24 French or less for delivery through a patient's vasculature on a catheter or equivalent mechanism.

When the valve member is mounted to the partially collapsed frame, the diameter of the valve member is greater than the diameter of the partially collapsed frame. For instance, in certain implementations, the diameter of the valve member is twice that of the partially collapsed frame. The valve member therefore cannot conform to the shape of the partially collapsed frame, and as a result, assembly of the valve assembly is rendered more difficult. Various techniques therefore can be utilized to ensure that the valve member is connected to the frame in a manner that when the frame is expanded, the valve member can assume its functional shape.

In one approach, a flexible skirt is used as an aid for mounting the valve member. The skirt has visual indicia marking the locations along the length of the skirt for attaching the skirt to the inner surface of the frame. Such visual indicia can be for example, markings on the surface of the skirt, slits or apertures, sutures attached to the skirt, or a longitudinal edge of the skirt shaped to indicate the attachment locations. The skirt is first attached to the inner surface of the frame and then the valve member is attached to the inner surface of the skirt. The skirt and the valve member are connected to the frame such that when the valve assembly is expanded, the skirt and the portion of the valve member attached to the skirt substantially conform to the shape of the expanded frame.

In another approach, a folding device is used to fold or bend the valve member into an undulated shape having a diameter that is approximately equal to the diameter of the partially collapsed frame. In use, the valve member is placed in the folding device and is folded to a smaller diameter. The frame is placed around the folded valve member, which is then attached to the frame at the apexes of the folds contacting the frame. In another implementation, both the valve member and the skirt are placed in the folding device and folded to a smaller diameter. The frame is then placed around the folded skirt and valve member, which are then attached to the frame. In another implementation, the folding device can be used to fold the skirt, which is then attached to the frame. The partially assembled valve is then removed from the folding device and the valve member is mounted to the frame.

In one representative embodiment, a method is provided for assembling an implantable prosthetic valve comprising a crimpable frame and valve member. The method comprises connecting the valve member to an inner surface of the frame member while a portion of the frame is at least partially crimped, with the partially crimped frame portion having a diameter that is less than the diameter of the valve member when the valve member is expanded to its functional size.

In another representative embodiment, a method of assembling an implantable prosthetic valve assembly comprises forming an annular frame in a partially crimped state, and mounting a flexible valve member to an inner surface of the partially crimped frame having a diameter that is less than the diameter of the valve member when expanded to its functional size.

In another representative embodiment, a method of percutaneous heart valve replacement comprises assembling a heart valve assembly by connecting a valve member to an expandable support stent when the stent is in a partially collapsed state having a first diameter. The method further comprises storing the heart valve assembly with the stent in the partially collapsed state, compressing the valve assembly just prior to implantation to a collapsed state having second diameter that is less than the first diameter, delivering the valve assembly to a native valve site of a patient through the patient's vasculature, and expanding the valve assembly at the native valve site to an expanded state having a third diameter that is greater than the first diameter.

In yet another representative embodiment, a prosthetic valve assembly comprises a frame that is radially compressible to a compressed state for percutaneous delivery of the valve assembly and radially expandable to an expanded state for operation of the valve assembly. The frame comprises first and second frame portions connected end-to-end, with each frame portion comprising a plurality of circumferential struts formed with multiple bends. The bends of the first frame portion have angles that are less than the angles of the bends of the second frame portion when the frame is in the expanded state. A valve member can be mounted to the frame when the first frame portion is in an expanded state and the second frame portion is in a partially collapsed state. For example, a base portion of the valve member can be attached to the expanded first frame portion and the commissure tabs of the valve member can be attached to the first and second frame portions.

In still another representative embodiment, a folding apparatus for use in mounting a prosthetic valve on a stent is configured to fold the valve into an undulated shape having multiple angularly-spaced, radially extending folds and a diameter that is less than the diameter of the expanded valve and stent.

The foregoing and other features and advantages of the invention will become more apparent from the following detailed description, which proceeds with reference to the accompanying figures.

BRIEF DESCRIPTION OF THE DRAWINGS

FIGS. 3A-3C show the frame of the heart valve assembly of FIG. 2 in a partially compressed state (FIG. 3A), an expanded state (FIG. 3B), and a compressed state (FIG. 3C).

FIG. 4 is a perspective view of the heart valve assembly of FIG. 2 shown prior to the valve member being mounted to the assembly.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

As used herein, the "expanded" or "deployed" state of a valve assembly or frame refers to the state of the valve assembly/frame when radially expanded to its functional size. The "crimped" or "compressed" state of a valve assembly or frame refers to the state of the valve assembly/frame when radially compressed to a diameter suitable for delivering the valve assembly through a patient's vasculature on a catheter or equivalent mechanism. A valve assembly/frame that is "partially crimped" or "partially compressed" has a diameter that is less than the diameter of the valve assembly/frame in the expanded state and greater than the diameter of the valve assembly/frame in the compressed state. In particular embodiments, the diameter of the partially crimped valve assembly is about two times greater than the compressed diameter and the expanded diameter is about 1.5 times greater than the partially crimped diameter. In an exemplary embodiment, the expanded diameter of the valve assembly is about 23 mm, the partially crimped diameter is about 15 mm, and the compressed diameter is about 7 mm (about 22 French).

Figure 2:
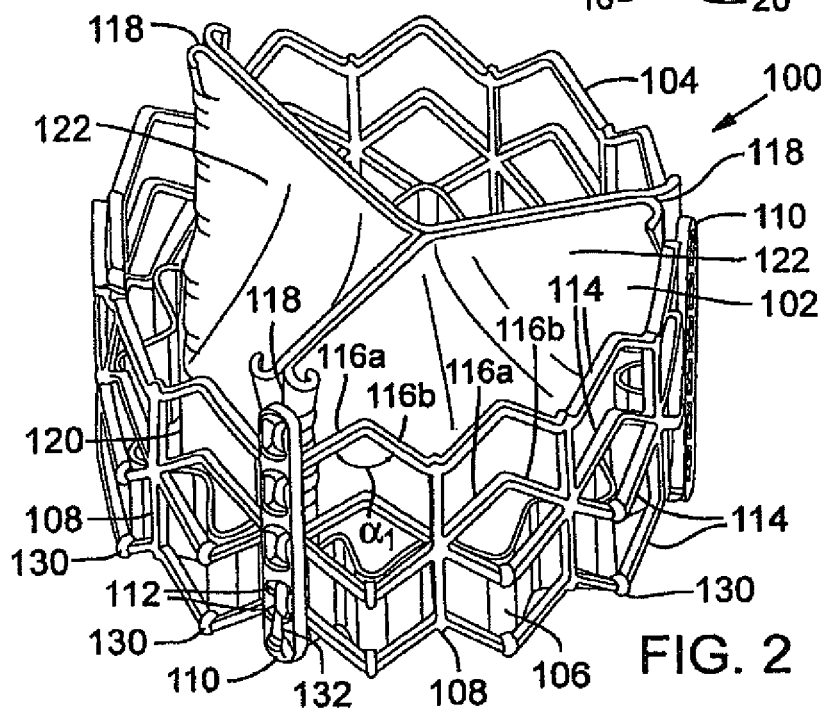
FIG. 2 is a perspective view of a percutaneous heart valve assembly shown in a partially compressed state, according to one embodiment.

FIG. 2 shows a first embodiment of an expandable, percutaneous prosthetic heart valve assembly 100 in a partially collapsed or crimped state. The valve assembly 100 is suitable for crimping into a narrow configuration for positioning and expandable to a wider, deployed configuration so as to anchor the assembly in position at the desired target location in the body (e.g., at the aortic annulus). The valve assembly 100 in the illustrated embodiment comprises a flexible valve member 102 (also referred to herein in other embodiments as a valve) mounted on an expandable, annular support stent, or frame, 104. The valve member 102 is mounted to the frame 104 when the frame 104 is in the partially collapsed state shown in FIG. 2. A flexible skirt 106 can be situated between the outer surface of valve member 102 and the inner surface of the frame 104. The skirt 106 can be used to facilitate mounting of the valve member 102 to the frame 104, as described in detail below.

The frame 104 in the illustrated embodiment comprises a plurality of angularly-spaced axial struts, or support members, 108 that extend axially (longitudinally) of the frame and a plurality of support posts, or beams, 110 spaced in the illustrated example at 120-degree intervals from each other around the frame 104. The support posts 110 can be formed with apertures 112 to facilitate mounting of the valve member 102 to the posts 110 such as by suturing the valve member 102 to the posts. The frame 104 can also include a plurality of axially-spaced, circumferential bands, or struts, 114 attached to the axial struts 108 and the support posts 110. The struts 114 are formed with multiple bends that allow the frame 104 to be crimped to a smaller diameter for delivery to an implantation site and expanded to a larger diameter for anchoring the valve assembly at the implantation site. For example, each of the struts 114 in the illustrated configuration includes a plurality of linear strut members 116a, 116b arranged in a zig-zag or saw-tooth configuration defining bends between adjacent strut members.

In alternative embodiments, the frame can have other configurations. For example, one or more of the circumferential bands 114 can have a curved or serpentine shape rather than a zig-zag shape. Further, the frame 104 can include various attachment elements (not shown), such as barbs, staples, flanges, and the like for enhancing the ability of the frame to anchor to the host tissue.

The frame 104 can be made from any of various suitable expandable and/or elastic materials and is typically made of a metal, such as stainless steel, titanium, or other biocompatible metals. The frame 104 also can be made from a shape memory alloy such as nickel titanium (NiTi) shape memory alloys, as marketed, for example, under the trade name Nitinol. The skirt 106 can be made from any of various suitable biocompatible synthetic materials, such as woven polyester or polytetrafluoroethylene (PTFE).

The valve member 102 can have a leafed-valve configuration, such as the tricuspid valve configuration shown in the illustrated embodiment. The valve member 102 can be formed from three pieces of pliant material connected to each other at seams 118 (also referred to as commissure tabs) to form collapsible leaflets 122 and a base portion 120 (the lower portion of the valve member in FIG. 2). The valve member 102 can be connected to the skirt 106 at the base portion 120 of the valve member and to the posts 110 at the seams 118. Various other valve configurations also can be used. Examples of other valves that can be utilized are disclosed in U.S. Pat. Nos. 6,730,118, 6,767,362, and 6,908,481, which are incorporated herein by reference.

The valve member 102 can be made from biological matter, such as natural tissue, pericardial tissue (such as bovine, porcine or equine pericardium), a harvested natural valve or other biological tissue. Alternatively, the valve member 102 can be made from biocompatible polymers or similar materials.

FIGS. 3A-3C are schematic views showing the frame 104 in the partially collapsed state (FIG. 3A) for mounting the valve member 102 (FIG. 2) to the frame; a collapsed, or compressed, state (FIG. 3C) for delivering the valve assembly; and an expanded state (FIG. 3B) for anchoring the valve assembly at an implantation site. As shown, when the valve assembly 100 is assembled, the frame 104 has an initial diameter $D_1$, and can be crimped to a diameter $D_2$ that is less than $D_1$ and expanded to a diameter $D_3$ that is greater than $D_1$. In certain embodiments, for example, the diameter $D_1$ of the partially collapsed frame 104 is approximately twice the diameter $D_2$ of the collapsed frame and the diameter $D_3$ of the expanded frame is about 1.5 times greater than $D_1$. In an exemplary embodiment, $D_1$ is about 15 mm, $D_2$ is about 7 mm, and $D_3$ is about 23 mm. In certain embodiments, the frame 104 can be compressed to a diameter such that the strut members 116a, 116b are nearly vertical and parallel to axial struts 108.

In particular embodiments, the frame 104 is manufactured in the partially collapsed state shown in FIG. 3A and need not be expanded or collapsed prior to its attachment to the valve member 102. Initially, the strut members 116a, 116b define angles $\alpha_1$ in the partially collapsed state and increase to angles $\alpha_2$ when the frame is expanded. The angles $\alpha_1$ defined between adjacent strut members 116a, 116b of the partially collapsed frame are selected to allow for even and predictable crimping of the frame, yet provide sufficient strength and rigidity to the struts 114 when the frame is expanded to resist closing forces exerted on the frame (for example, the recoil force exerted on the frame by the distorted stenosed native valve orifice). For example, in certain implementations, the angles $\alpha_1$ of the partially collapsed frame are in the range of about 50 to about 90 degrees, with 70 degrees being a specific example, and the angles $\alpha_2$ of the expanded frame are in the range of about 90 to about 179 degrees, and more desirably in the range of about 90 to about 130 degrees, with 120 being a specific example.

As discussed above, known valve assemblies typically are assembled with the frame in an expanded state. With the frame in the expanded state, the valve member can be expanded to closely conform to the inner surface of the frame, such as by mounting the valve member on a cylindrical mandrel having a diameter slightly smaller than the diameter of the expanded frame. As a result, it is a relatively simple matter to attach the valve member to the frame, such as with sutures.

However, when attaching the valve member 102 to the frame 104 in the partially collapsed state, the diameter of the valve member 102 can be much greater than the diameter $D_1$ of the partially collapsed frame 104. The valve member 102 in such cases cannot conform to the shape of the partially collapsed frame, and as a result, assembly of the valve assembly is rendered more difficult. Accordingly, one or more of the following techniques can be employed to facilitate the assembly process.

Figure 5:
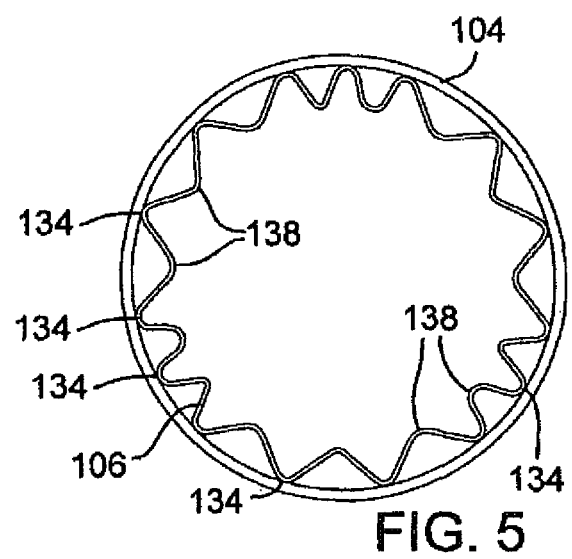
FIG. 5 is a top plan view of the partially assembled valve assembly shown in FIG. 4.

In one approach, for example, the flexible skirt 106 (FIGS. 2 and 4-6) is used as an attachment aid. When assembling the valve assembly 100, the skirt 106 is first attached to the inner surface of the frame 104, such as with sutures 130 or other suitable attachment techniques or mechanisms. The length of the skirt 106 (when laid flat) is approximately equal to the inner circumference of the frame 104 when expanded. As best shown in FIG. 5, the skirt 106 therefore is attached to the frame 104 at discrete, spaced-apart locations 134 around the periphery of the skirt such that the skirt 106 takes on an undulated shape with slack portions 138 between the connection locations remaining unattached to the frame. The spacing between the connection locations 134 is such that when the frame 104 is expanded, the skirt takes on a substantially tubular shape closely conforming in an abutting relationship with the inner surface of the frame. After attaching the skirt 106 to the frame 104, the base portion 120 of the valve member 102 can then be attached to the skirt 106 and/or the support posts 110, such as with sutures 132 (FIG. 2) or other suitable fasteners. The valve member 102 is placed in a partially crimped state but when the frame 104 is expanded, the base portion of the valve member expands to a tubular shape closely conforming to the inner surface of the skirt 106 in an abutting relationship.

Figure 6:
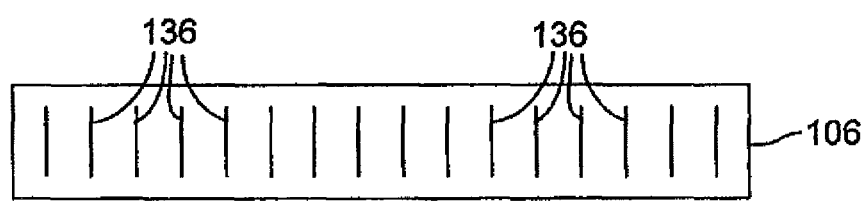
FIG. 6 is a plan view of an exemplary embodiment of a flexible skirt that can be used to attach a valve member to a frame.

As shown in FIG. 6, the skirt 106 (shown laid flat) can be provided with visual indicia along its length to identify the locations on the skirt for attaching the skirt to the frame 104. The visual indicia can be, for example, markings 136, slits or holes formed in the skirt, or sutures attached at spaced-apart locations along the length of the skirt. If sutures are used to mark the connecting locations, the sutures can also be used in connecting the skirt to the frame.

Figure 7:
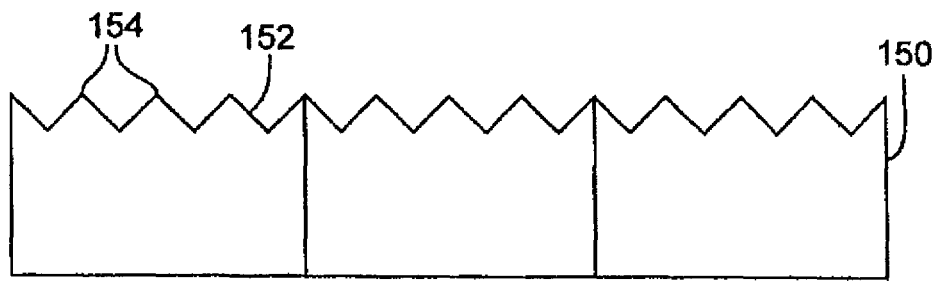
FIG. 7 is a plan view of another embodiment of a flexible skirt.

FIG. 7 shows a skirt 150, according to another embodiment. The skirt 150 is formed with a generally saw-tooth shaped edge 152 with apexes 154 marking the locations along the length of the skirt for attaching the skirt to the frame 104.

Figure 8:
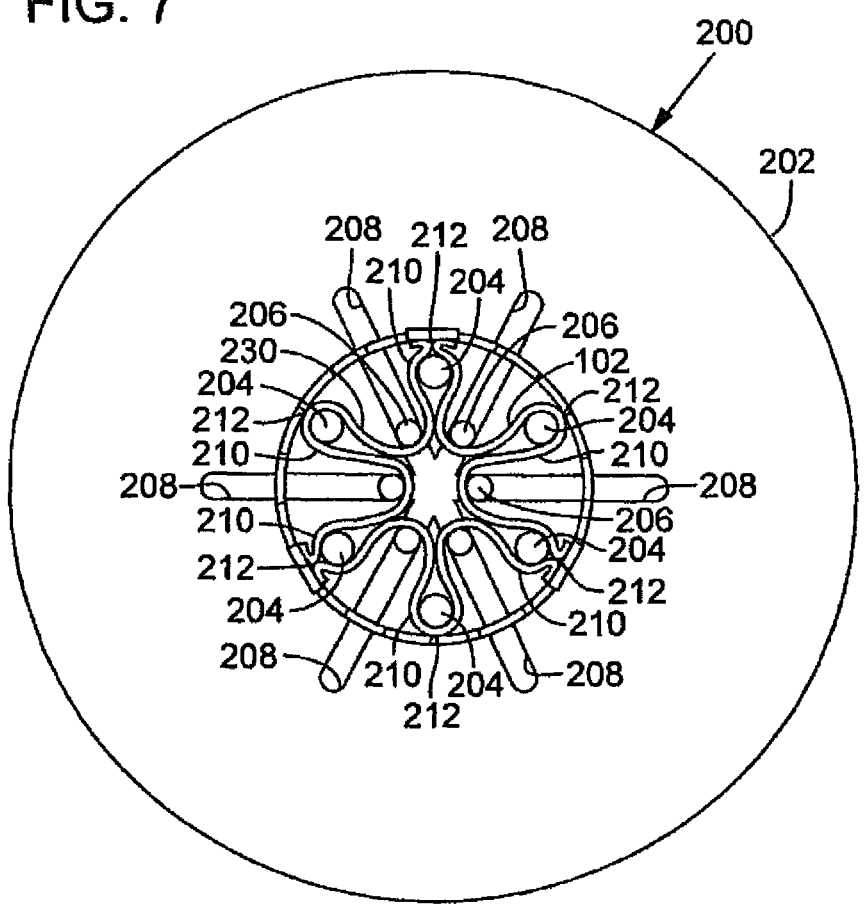
FIG. 8 is a top plan view of an exemplary embodiment of a folding apparatus for use in assembling a valve assembly shown with a valve member retained in a folded state and a frame placed around the folded valve member.
Figure 9:
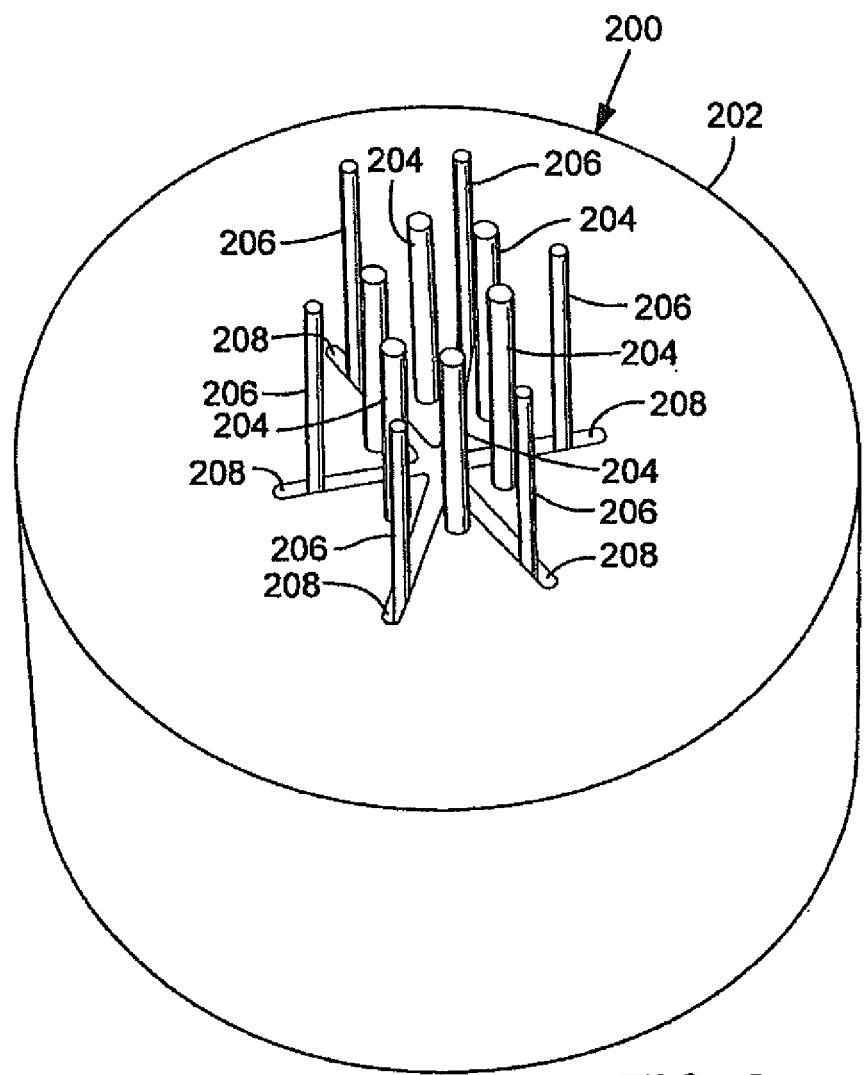
FIG. 9 is a perspective view of the folding apparatus.

In another approach for assembling the valve assembly 100, a folding device can be utilized to fold or bend the valve member 102 into an undulated shape for attaching the valve member 102 to the frame 104. FIGS. 8-12 show an exemplary embodiment of a folding device, indicated generally at 200. Referring to FIGS. 8 and 9, the folding device 200 in the illustrated embodiment can comprise an outer housing, or casing, 202, a plurality of fixed posts, or pins, 204, and a plurality of moveable posts, or pins, 206 extending from the housing 202. In this manner, the housing serves as a base or support for the posts 204, 206.

There are a total of six fixed posts 204 and a total of six moveable posts 206 in the illustrated embodiment, although the number of posts 204, 206 can vary in different applications. The fixed posts 204 can be mounted at fixed locations on the upper surface of the housing 202. The moveable posts 206 are slidable in respective radially extending slots 208 in the upper surface of the housing 202 so that the posts 206 can be moved radially toward and away from each other. The posts 204, 206 are angularly spaced around a center point C on the base 202 centrally located between the posts. The center point C in the illustrated embodiment coincides with the geometric center of the housing 202, although in other embodiments the center point C can be offset from the geometric center of the housing.

In use, the valve member 102 can be placed around the posts 204, 206 with the valve member 102 extending around the outside of the fixed posts 204 and the inside of the moveable posts 206 (FIG. 8). The posts 206 can then be moved radially inwardly toward each other to form multiple angularly-spaced, radially extending folds 210 in the valve member, as depicted in the FIG. 8. The folded valve member has a diameter (measured between diametrically opposing apexes 212) that is less than the diameter of the valve member in its expanded state. This allows the frame 104 (in the partially collapsed state) to be placed around and attached to the valve member 102 at the apexes 212 of the folds 210, such as by suturing the valve member to the frame at the apexes 212. As shown, the spacing between the fixed posts 204 and the center point C desirably is selected such that the partially collapsed frame 104 can contact the apexes 212 when placed around the folded valve member. Slack portions 230 of the folded valve member between the apexes 212 remain unattached to the frame 104. In certain embodiments, the apexes 212 of the folds are attached to the lower half of the frame 104 at the base portion 120 of the valve member and to the support posts 110 of the frame where the apexes 212 coincide with the seams of the valve member. Thus, when the frame 104 is expanded to its functional size, the base portion 120 of the valve member 102 expands to a tubular shape closely conforming to the inner surface of the frame in an abutting relationship.

The moveable posts 206 can be operatively connected to an adjustment mechanism that is operable to move posts 206 simultaneously such that the posts 206 are always equidistant from the center point C. In this manner, the folding device 200 can easily form substantially equal and symmetrical folds 210 in the valve member 102 without having to position individual posts 206.

Figure 10:
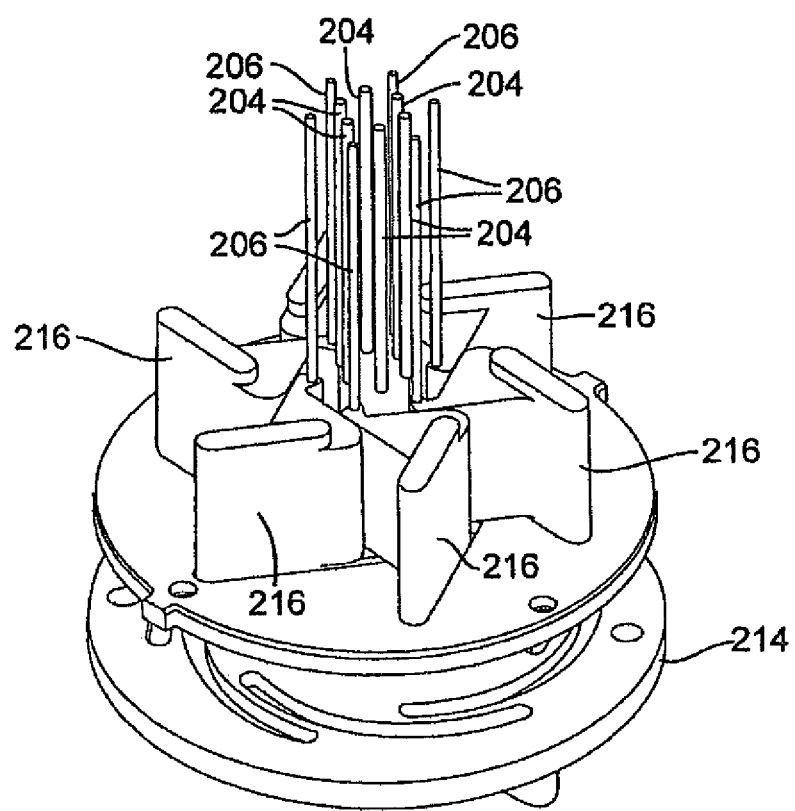
FIG. 10 is a partially exploded, perspective view of the folding apparatus shown with the housing removed.
Figure 11:
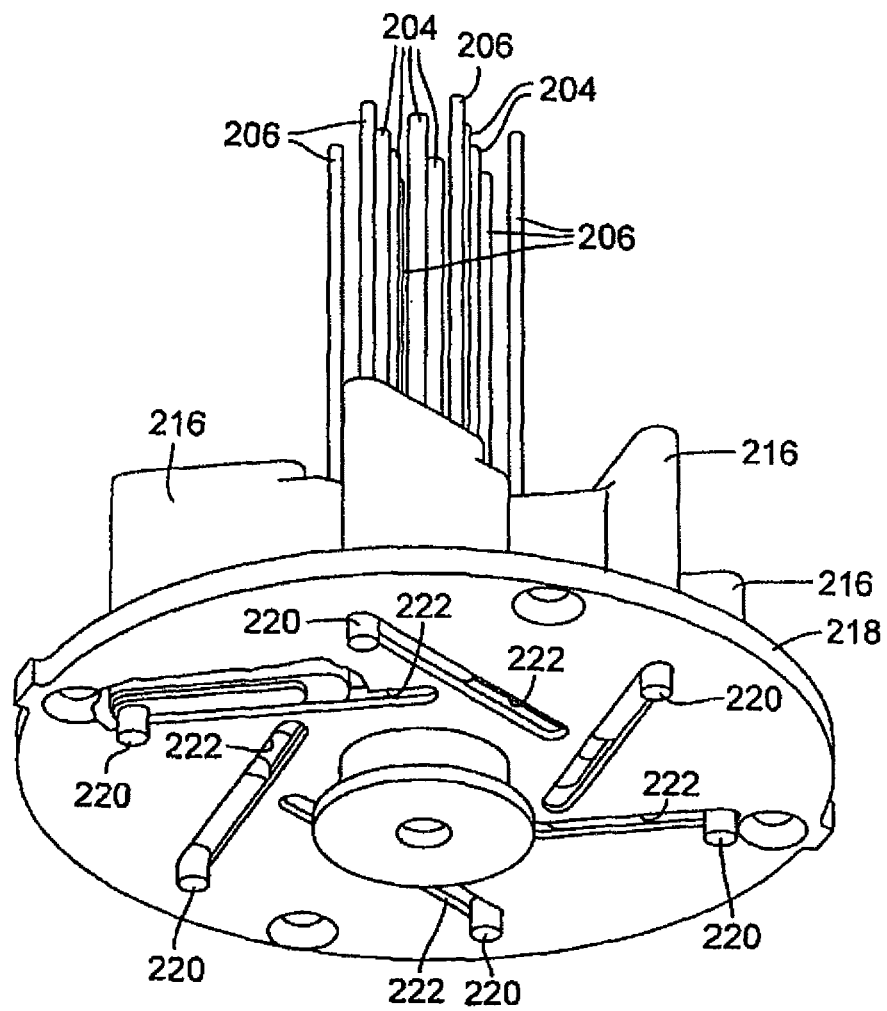
FIG. 11 is a perspective view of the support plate, bases and associated posts of the folding apparatus.
Figure 12:
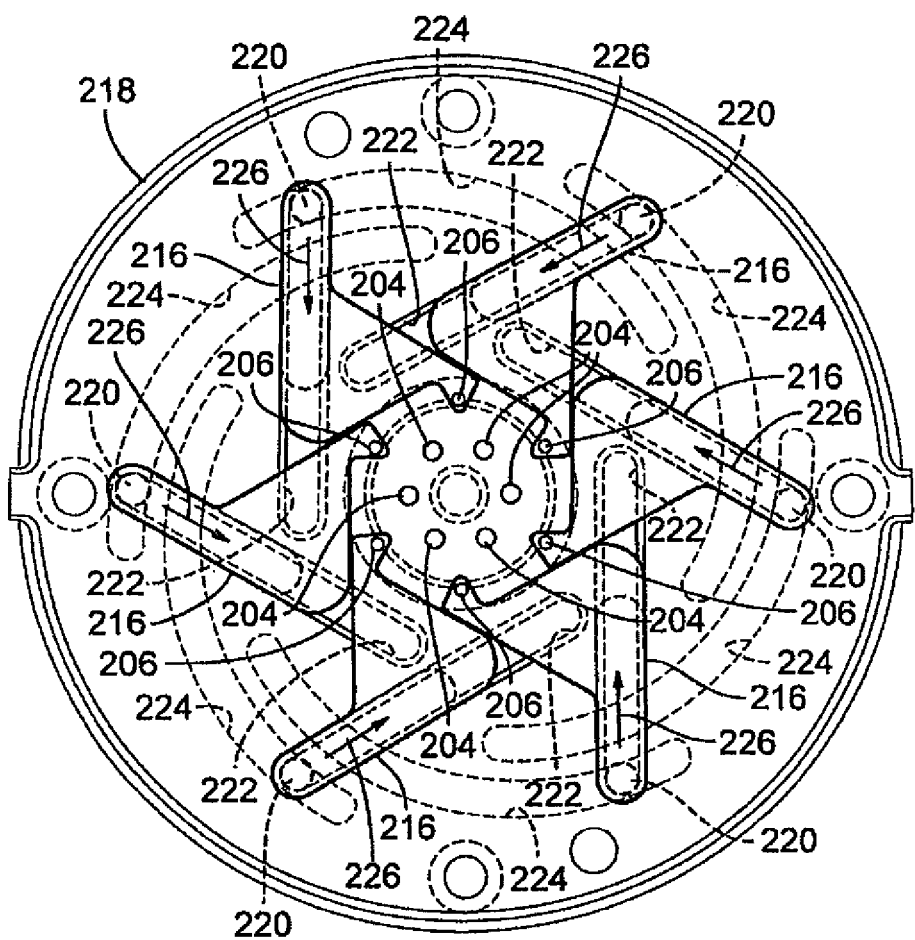
FIG. 12 is a top plan view of the folding apparatus shown with the housing removed.

For example, referring to FIGS. 10-12, the illustrated folding device 200 includes an adjustment mechanism 214 in the form of a circular plate positioned at the bottom of the folding device. The moveable posts 206 are mounted to respective bases 216, which are supported on a support plate 218 inside the housing 202. As shown in FIG. 11, each base 216 is provided with a downwardly projecting pin 220, each of which extends through a respective linear slot 222 formed in the support plate 218. As best shown in FIG. 12, the slots 222 are equally dispersed around the center point C of the device with each slot extending in a direction that is offset from the center point C by the same distance. The bottom plate 214 is formed with a plurality of arcuate slots 224, each of which receives the bottom end portion of a respective pin 220 of a base 216. The slots 224 are equally dispersed around the center point C with the center of curvature of each slot 224 being offset from the center point C by the same distance.

By virtue of the arrangement of the slots 208, 222, 224, rotation of the bottom plate 214 is effective to move the posts 206 simultaneously toward or away from each other. For example, referring to FIG. 12, rotating the bottom plate 214 counterclockwise causes the pins 220 to move within their respective slots 222 (in the directions indicated by arrows 226), which in turn causes each base 216 to move in the same direction. The bases 216 in turn move their respective pins 206 radially inwardly toward each other to create the folds 210 in the valve member 102 (FIG. 8). Rotating the bottom plate 214 clockwise in FIG. 12 causes the bases 216 to move in the opposite direction, which in turn causes the posts 206 to move simultaneously radially outwardly from each other.

In another approach for assembling the valve assembly 100, the folding device 200 can be used to fold the skirt 106, which can then be attached to the frame 104 at the apexes of the folds contacting the frame. The frame 104 and skirt 106 are then removed from the folding device and the valve member 102 can be attached to the inner surface of the skirt 106.

In certain embodiments, the valve assembly 100 can be assembled prior to storage. Just prior to implantation, the valve assembly is removed from the storage container, placed on the end portion of a delivery catheter and radially crimped about the catheter for percutaneous delivery. Alternatively, the components of the valve assembly can be stored separately and assembled in the operating theater just prior to implantation. A conventional crimping device can be used to crimp the valve assembly on the catheter. One such crimping device is described in U.S. Pat. No. 6,730,118.

Various procedures can be employed for delivering and deploying the valve assembly at a target site, as described for example in the '118 patent. In one implementation, for example, the valve assembly is mounted on an inflatable balloon of a flexible catheter and inserted into the patient's vasculature via an introducer sheath or other cannula. The valve assembly is advanced through the patient's vasculature while mounted on the balloon until it reaches the desired target location (for example, at the aortic annulus in the case of an aortic valve assembly). The balloon is then inflated and the valve assembly expands radially, anchoring the frame to the surrounding tissue.

In another implementation, the frame 104 can be made of a self-expanding material and the valve assembly can be mounted in a crimped state on the end of a catheter with a sheath over the valve assembly. The valve assembly is advanced through the patient's vasculature until it reaches the desired target location, at which point the sheath is retracted from the valve assembly to allow the frame to expand and engage the surrounding tissue. In another implementation, the valve assembly can be implanted in an open-heart procedure with the valve assembly being delivered to the target site using a valve holder, as known in the art.

Figure 13:
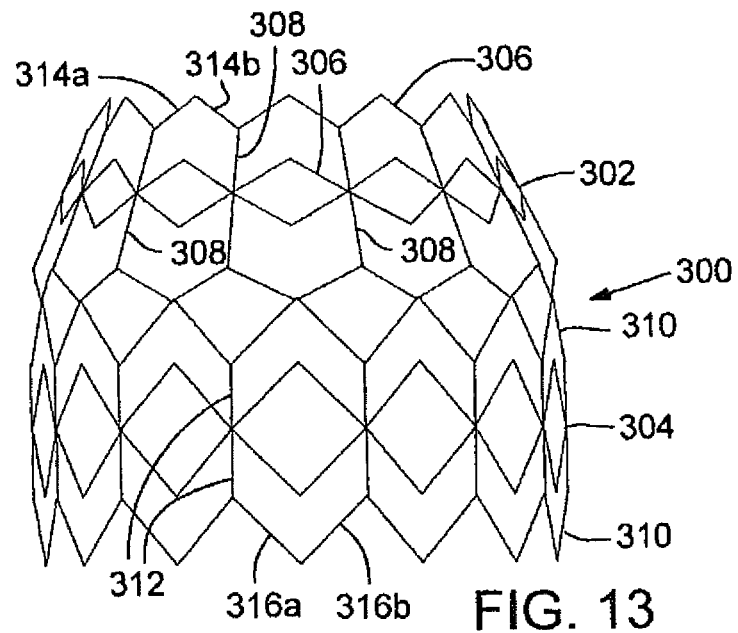
FIG. 13 is a side elevation view of a radially compressible and expandable frame for a prosthetic valve assembly shown with an upper frame portion in a partially collapsed state and a lower frame portion in an expanded state, according to another embodiment.
Figure 14:
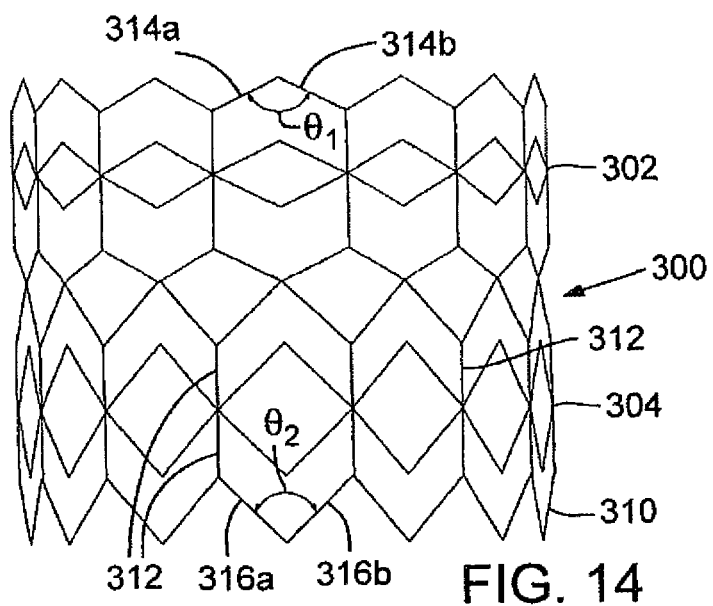
FIG. 14 is a side elevation view of the frame of FIG. 13 shown with both frame portions in expanded states.

FIGS. 13 and 14 illustrate another embodiment of an expandable and collapsible frame 300 of a heart valve assembly. FIG. 13 shows the frame 300 in a partially collapsed state for mounting a valve member (e.g., valve member 102). FIG. 14 shows the frame 300 expands to its functional size. The frame 300 includes a first frame portion 302 connected end-to-end to a second frame portion 304. The valve member (not shown in the drawings) is connected to the second frame portion 304, which exhibits better crimpability than the first frame portion 302. The first frame portion 302, on the other hand, has a more rigid construction than the second frame portion 304, and therefore enhances the overall strength and rigidity of the frame 300. Prior to implantation, both frame portions 302, 304 can be crimped to a smaller diameter from the partially collapsed state shown in FIG. 13. When the valve assembly is positioned at the target site in a patient, the frame portions 302, 304 are expanded to their functional size, as shown in FIG. 14.

The first frame portion 302 includes a plurality of circumferential, zig-zag struts 306 connected to a plurality of axial struts 308. The struts 306 comprise a plurality of linear strut members 314a, 314b, with each adjacent pair of strut members connected to each other at an angle $\theta_1$ in the expanded state (FIG. 14). Similarly, the second frame portion 304 includes a plurality of circumferential, zig-zag struts 310 connected to a plurality of axial struts 312. The struts 310 comprise a plurality of linear strut members 316a, 316b, with each adjacent pair of strut members connected to each other at an angle $\theta_2$.

Figure 1:
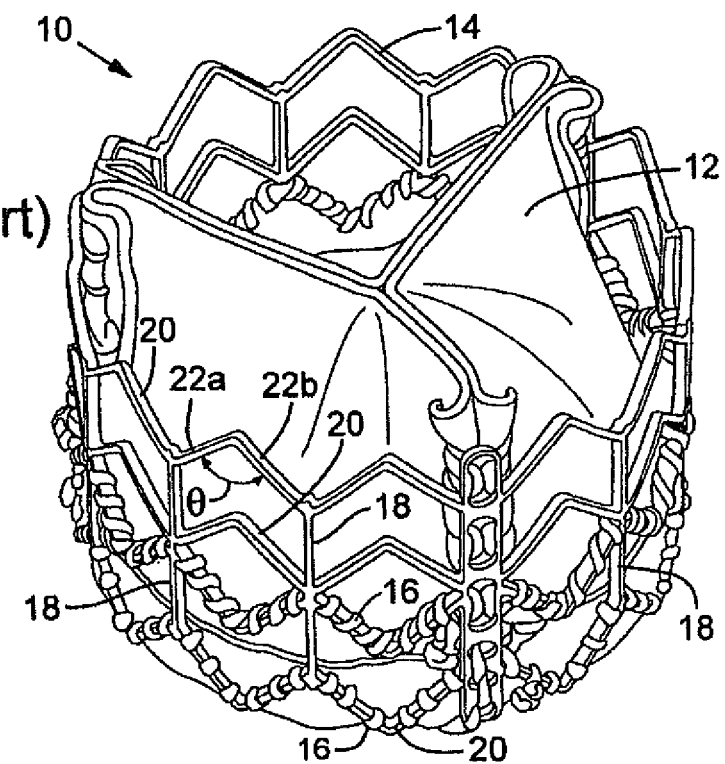
FIG. 1 is a perspective view of a prior art prosthetic heart valve assembly configured for percutaneous introduction.

The frame 300 is formed in the partially collapsed state (FIG. 13) with the second frame portion 304 at its functional size and the first frame portion 302 having a frusto-conical shape tapering from a first diameter at the end connected to the second frame portion to a second, smaller diameter at the opposite end. In this state, the second frame portion 304 has an inner diameter approximately equal to the outer diameter of the valve member so that the valve member can be easily attached to the second frame portion 304 using conventional techniques or mechanisms. For example, the valve member can be sutured to the second frame portion 304, similar to the valve assembly shown in FIG. 1.

Alternatively, the base portion of the valve member can be attached to the second frame portion 304 around its circumference while the commissure tabs can be attached to both the first and second frame portions. In this alternative embodiment, the frame 300 can have an overall length (measured in the axial direction) that is approximately equal to or slightly greater than the valve member.

The angles $\theta_2$ between strut members 316a, 316b are selected to permit even and predictable crimping of the frame portion 304. In particular embodiments, for example, angles $\theta_2$ are in the range of about 80 degrees to about 110 degrees, with 100 degrees being a specific example. In this manner, the second frame portion 304 with the valve member mounted thereon can have a construction that is similar to the valve assembly shown in FIG. 1.

The angles $\theta_1$ between strut members 314a, 314b of the first frame portion 302 when expanded are greater than the angles $\theta_2$, and in particular embodiments the angles $\theta_1$ are in the range of about 90 degrees to about 130 degrees, with about 120 degrees being a specific example. In this manner, the first frame portion 302 serves as the primary structural component of the frame 300 to enhance the rigidity of the frame and better resist closing forces on the valve assembly once it is implanted. Due to the first frame portion 302 being in a partially crimped state when the valve member is attached (FIG. 13), it can be more easily crimped to the fully crimped state for delivering the valve assembly through the patient's vasculature.

Figure 15:
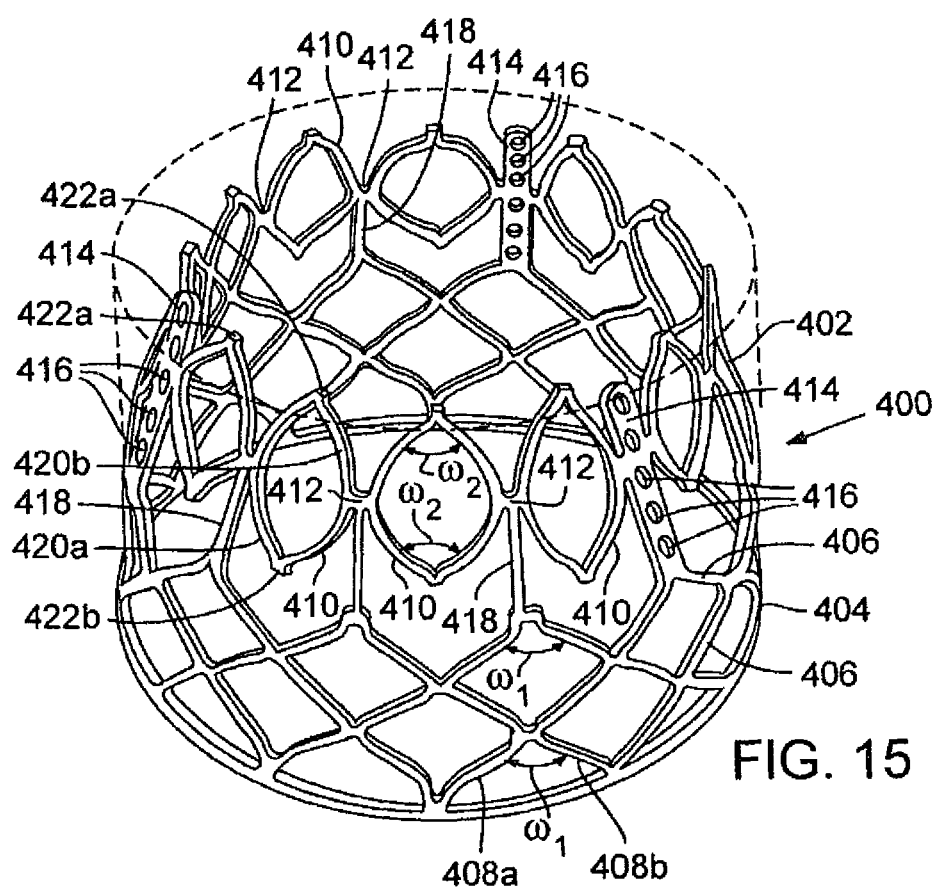
FIG. 15 is a perspective view of a radially compressible and expandable frame shown with a first frame portion in a partially crimped condition, according to another embodiment.

FIG. 15 illustrates another embodiment of an expandable and collapsible frame 400 of a heart valve assembly. FIG. 15 shows the frame 400 in a partially collapsed state for mounting a valve member (e.g., valve member 102). The frame 400 includes a first frame portion 402 connected end-to-end to a second frame portion 404. The frame 400 is formed in the partially collapsed state with the second frame portion 404 at its expanded, functional size, while the first frame portion 402 is partially crimped and has a frusto-conical shape tapering from a first diameter at the end connected to the second frame portion to a second, smaller diameter at the opposite end. In this state, a valve member (e.g., valve member 102) can be attached to the first frame portion 402 and/or the second frame portion 404, such as by suturing the valve member to the frame.

The first frame portion 402 serves as the primary structural component of the frame 400 and is generally more rigid than the second frame portion 404 once the frame is deployed. However, the geometry of the first frame portion 402 is generally less stable under crimping than the second frame portion 404 and therefore is formed in the partially crimped state shown in FIG. 15 so that it can be more easily crimped to a fully crimped state on a delivery catheter. In certain embodiments, the frame portions 402, 404 are constructed such that when both are expanded, the struts of the first frame portion 402 have bends defining angles that are greater than the struts of the second frame portion 404.

The second frame portion 404 in the illustrated embodiment has a plurality of axially-spaced, circumferential struts 406, each of which includes a plurality of linear strut members 408a, 408b arranged in a zig-zag or saw-tooth configuration defining angles $\omega_1$ between adjacent strut members. As shown, the second frame portion 404 in particular embodiments does not include axial or vertical strut members. Due to the absence of axial strut members, this geometry is generally more stable and less susceptible to buckling during crimping. Consequently, the second frame portion 404 can be formed with obtuse angles $\omega_1$ to enhance the overall structural rigidity of the frame once implanted. For example, in exemplary embodiments, the angles $\omega_1$ are in the range of about 91 degrees to about 110 degrees, with about 100 degrees being a specific example. In alternative embodiments, however, the second frame portion 404 can be formed with angles $\omega_1$ that are 90 degrees or less.

The first frame portion 402 in the illustrated embodiment comprises a plurality of generally ring-shaped structures or cells 410 connected to each other at junctures 412 to form a circumferentially extending band. The first frame portion 402 can include angularly-spaced support posts, or beams, 414 spaced, for example, at 120-degree intervals from each other around the frame. The support posts 414 can be formed with apertures 416 to facilitate mounting of a valve member to the posts 414 such as by suturing the valve member to the posts. The lower end of each post 414 can be connected to the uppermost circumferential strut 406 of the second frame portion at the junction of two strut members 408a, 408b to interconnect the first and second frame portions. The first frame portion 402 can also be interconnected to the second frame 404 by axial strut members 418, each connected to and extending between a juncture 412 and the uppermost circumferential strut 406 at the junction of two strut members 408a, 408b.

Each cell 410 in the illustrated configuration is formed by first and second arcuate strut members 420a, 420b, respectively, that intersect at upper and lower junction points 422a, 422b, respectively. The strut members 420a, 420b of each cell 410 define first and second angles $\omega_2$. When expanded to its functional size, the first frame portion 402 expands radially to a generally cylindrical shape (indicated by the dashed outline in FIG. 15), causing the angles $\omega_2$ to increase. In particular embodiments, the angles $\omega_2$ of the first frame portion 402 in the partially crimped state are in the range of about 70 degrees to about 100 degrees, with 90 degrees being a specific example. When the first frame portion 402 is expanded to its functional size, the angles $\omega_2$ between the strut members 420a, 420b are in the range of about 90 degrees to about 130 degrees, with about 120 degrees being a specific example.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A percutaneous prosthetic heart valve assembly having enhanced rigidity, comprising:
    a radially compressible and expandable support stent, the support stent having a compressed state with a compressed diameter for percutaneous delivery of the prosthetic heart valve assembly to an implantation site, the support stent having an expanded state with an expanded diameter for operation of the prosthetic heart valve assembly at the implantation site, the support stent further having a partially collapsed state with a partially collapsed diameter that is between the compressed and expanded diameters for attachment of a valve member and storage of the assembly, the support stent formed with a plurality of circumferential bands, each band comprising a plurality of linear strut members forming a zig-zag configuration, wherein when the support stent is in the partially collapsed state adjacent strut members form angles of between about 50-90°, and in the expanded state adjacent strut members form angles of about 90-179° for enhanced rigidity when the support stent is in the expanded state; and
    a flexible valve member coupled to the support stent in the partially collapsed state, wherein the valve member has an expanded configuration suitable for functioning as a one-way valve with a corresponding diameter that matches the expanded diameter of the support stent, and attaches at spaced locations within the support stent when the support stent is in the partially collapsed state with locations therebetween that are out of contact with the stent.

2. The prosthetic heart valve assembly of claim 1, further comprising a flexible skirt positioned between the support stent and the flexible valve member, wherein the skirt is sutured to the support stent and the valve member is sutured to the skirt.

3. A method for deploying the valve assembly of claim 1 at a native valve site of a patient, the method comprising:
    mounting the prosthetic heart valve assembly in the compressed state on a flexible catheter;
    guiding the catheter through the patient's vasculature to the native valve site; and
    expanding the prosthetic heart valve assembly to cause the support stent to become anchored to the native valve site.

4. The prosthetic heart valve assembly of claim 2, wherein in the partially compressed state of the support stent, the flexible skirt includes multiple angularly-spaced, radially extending folds having outer apices that are attached to the support stent.

5. The prosthetic heart valve assembly of claim 2, wherein the flexible skirt has visual indicia marking spaced attachment locations along the length of the skirt to indicate locations for attaching the skirt to the inner surface of the support stent.

6. The prosthetic heart valve assembly of claim 5, wherein the visual indicia are selected from the group consisting of: markings, slits or apertures, sutures attached to the skirt, and a longitudinal edge of the skirt shaped to indicate the attachment locations.

7. The prosthetic heart valve assembly of claim 5, wherein the flexible skirt is formed with a generally saw-tooth shaped circumferential edge to indicate the attachment locations.

8. The prosthetic heart valve assembly of claim 1, wherein the partially collapsed diameter is approximately mid-way between the compressed and expanded diameters.

9. The prosthetic heart valve assembly of claim 8, wherein the partially collapsed diameter is about two times the compressed diameter, and the expanded diameter is about 1.5 times the partially collapsed diameter.

10. The prosthetic heart valve assembly of claim 9, wherein the expanded diameter is about 23 mm, the partially collapsed diameter is about 15 mm, and the compressed diameter is about 7 mm.

11. The prosthetic heart valve assembly of claim 1, wherein when the support stent is in the partially collapsed state the flexible valve member is folded within the support stent so as to have an undulating shape with outer fold apexes that contact and attach to the support stent.

12. The prosthetic heart valve assembly of claim 11, wherein the valve member has slack portions between outer fold apexes that remain out of contact with the support stent, and wherein when the support stent is expanded to the expanded state, the valve member assumes a tubular cross-sectional profile within the support stent.

13. The prosthetic heart valve assembly of claim 1, wherein the support stent is balloon-expandable.

14. The prosthetic heart valve assembly of claim 1, wherein the support stent is self-expandable.

15. The prosthetic heart valve assembly of claim 1, wherein the support stent further comprises a plurality of support beams spaced at about 120-degree intervals from each other around the support stent and connected to each of the circumferential bands, the support beams being formed with apertures to mount the flexible valve member by suturing to the beams.

16. The prosthetic heart valve assembly of claim 1, wherein the support stent comprises a first frame portion connected end-to-end to a second frame portion, and the flexible valve member is connected to the second frame portion, wherein the first frame portion has a more rigid construction than the second frame portion.

17. The prosthetic heart valve assembly of claim 1, wherein when the support stent is in the partially collapsed state, adjacent strut members form angles that render the circumferential bands nearly circular.

18. A percutaneous prosthetic heart valve assembly comprising:
a frame that is radially compressible to a compressed state for percutaneous delivery of the valve assembly and radially expandable to an expanded state for operation of the valve assembly at the implantation site, the frame comprising first and second frame portions connected end-to-end, each frame portion comprising a plurality of circumferential struts, each strut formed with multiple bends, and
a flexible valve member connected to the second frame portion,
and wherein the frame has a partially collapsed state with the first frame portion having a partially collapsed diameter that is between the diameters of the first frame portion in its compressed and expanded states and where the second frame portion is in its expanded state having an inner diameter approximately equal to an outer diameter of the valve member, and in the partially collapsed state of the frame the bends of the first frame portion having angles $\theta_1$ that are less than angles $\theta_2$ of the bends of the second frame portion.

19. The prosthetic heart valve assembly of claim 18, wherein in the partially collapsed state of the frame the first frame portion has a frusto-conical shape tapering from a first diameter at an end connected to the second frame portion to a second, smaller diameter at the opposite end.

20. The prosthetic heart valve assembly of claim 18, wherein in the partially collapsed state the second, smaller diameter of the first frame portion is approximately mid-way between the compressed and expanded diameters of the frame.

21. The prosthetic heart valve assembly of claim 18, wherein the first frame portion has a more rigid construction than the second frame portion.

22. The prosthetic heart valve assembly of claim 18, wherein 90 degrees $<\theta_1 <179$ degrees.

23. The prosthetic heart valve assembly of claim 18, further comprising a flexible skirt positioned between the second frame portion and the flexible valve member, wherein the skirt is sutured to the second frame portion and the valve member is sutured to the skirt.

24. The prosthetic heart valve assembly of claim 18, wherein the frame is balloon-expandable.

25. The prosthetic heart valve assembly of claim 18, wherein the frame is self-expandable.

26. The prosthetic heart valve assembly of claim 18, wherein the second frame portion further comprises a plurality of support beams spaced at about 120-degree intervals from each other around the second frame portion and connected to each of the circumferential struts, the support beams being formed with apertures to mount the flexible valve member by suturing to the beams.

* * * * *